United States Patent [19]
Greene

[11] 3,958,693
[45] May 25, 1976

[54] VACUUM X-RAY ENVELOPE
[75] Inventor: Franklin R. Greene, Flushing, N.Y.
[73] Assignee: E-Z-EM Company Inc., Westbury, N.Y.
[22] Filed: Jan. 20, 1975
[21] Appl. No.: 542,256

[52] U.S. Cl................................. 206/455; 150/9; 206/808; 250/475; 229/62.5
[51] Int. Cl.² .................. B81D 81/20; B03B 41/18
[58] Field of Search.................... 206/454, 808, 455; 229/62.5, 48 T; 250/477, 475, 480; 150/9; 137/223; 53/22 B, 22 R, 12

[56] References Cited
UNITED STATES PATENTS

| | | | |
|---|---|---|---|
| 2,371,843 | 3/1945 | Powers | 250/480 |
| 2,764,859 | 10/1956 | Hanselmann | 53/22 B |
| 3,233,101 | 2/1966 | Forsyth | 250/475 |

Primary Examiner—William T. Dixson, Jr.
Attorney, Agent, or Firm—Ryder, McAulay, Fields, Fisher & Goldstein

[57] ABSTRACT

An opaque vinyl envelope having facing polished inner surfaces and an open edge into which an intensifier screen and X-ray film are inserted. The other three edges are completely sealed except for a valve at one edge. Reinforcing strips are attached along the open edge. The three sealed edges of the envelope are heat sealed without pressure to eliminate an internal bead and minimize leakage along the bead when the open edge is closed and the envelope evacuated. An insert that has a relatively rough surface or is porous assures full evacuation.

10 Claims, 7 Drawing Figures

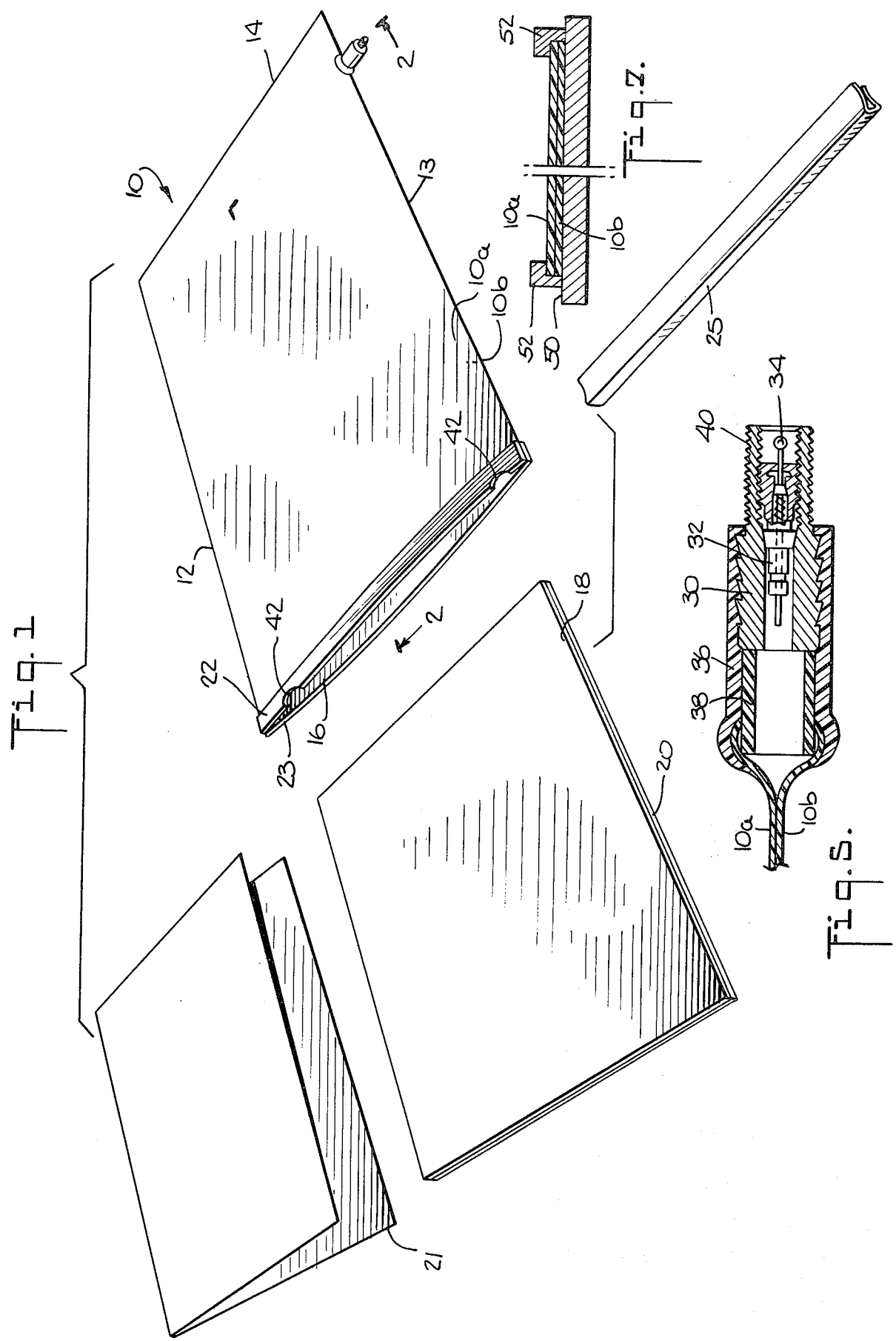

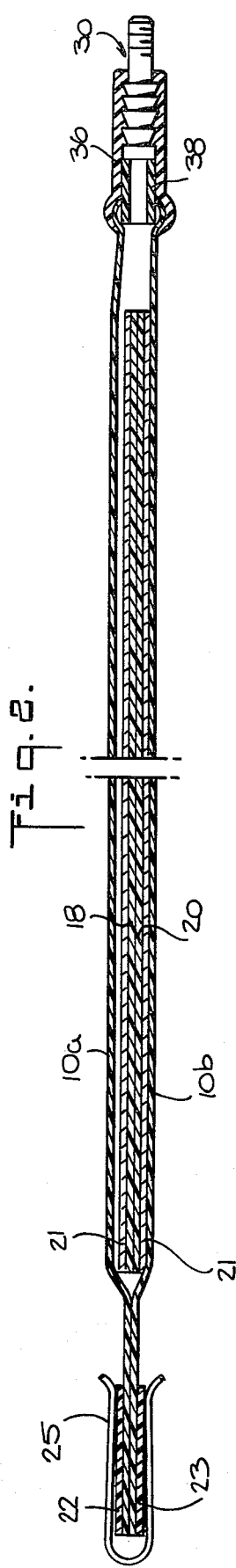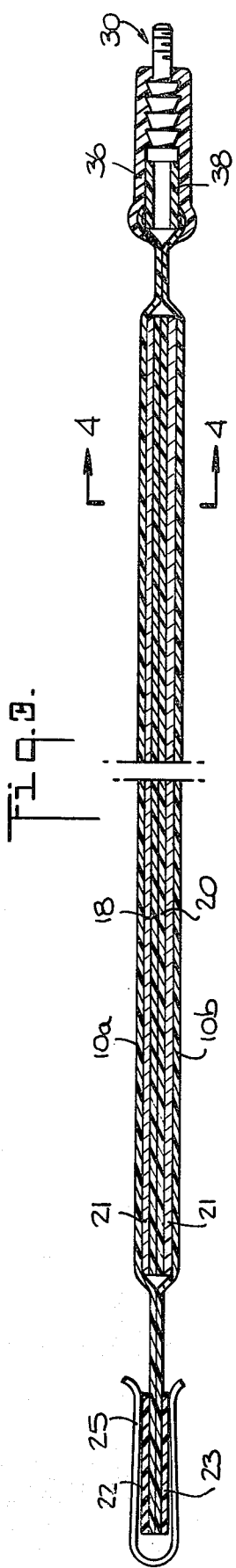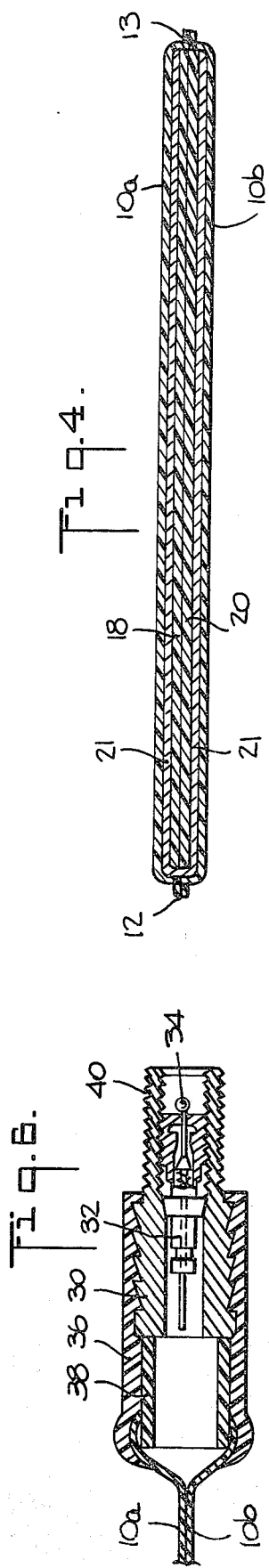

VACUUM X-RAY ENVELOPE

REFERENCE TO RELATED APPLICATION

This application is a continuation-in-part to co-pending patent application Ser. No. 438,033 filed Jan. 30, 1974.

BACKGROUND OF THE INVENTION

This invention relates in general to a vacuum cassette to be used in the taking of X-rays where an intensifier screen is employed.

When taking an X-ray, it is known to place the unexposed film next to an intensifier screen so as to increase contrast and thus make possible lower X-ray intensity to minimize patient exposure to X-rays. To obtain effective use of the intensifier, it is important that the unexposed X-ray film be held tightly against the intensifier screen. It is known to achieve this result by placing the film and intensifier screen together in a vinyl envelope, apply a vacuum to the inside of the envelope to collapse the sides of the envelope onto the X-ray film and intensifier screen thereby holding film and screen tightly together. While the vacuum is applied, the open edge of the envelope is heat or pressure sealed and the resulting four-ply sandwich is then ready for use. This loading of the envelope, application of vacuum and sealing must all take place in a darkroom so that the film is not exposed during the process. Special equipment for use in the darkroom is required to effect this known process and the envelope employed can only be used once.

It is a purpose of this invention to provide a simpler, less time consuming and less expensive technique for producing the vacuum cassette.

A further purpose of this invention is to provide a technique which permits reusing the envelope.

Another purpose to this invention is to provide a structure that assures full evacuation across the entire face of the X-ray film and intensifier screen.

BRIEF DESCRIPTION OF THE INVENTION

In brief, this invention is in an opaque vinyl envelope having interior polished faces and an open edge into which the intensifier screen and X-ray film are inserted. The other three edges are completely sealed except for a valve preferably located at a side edge near a corner removed from the open edge. A separate reinforcing strip is attached to each envelope sheet along the open edge. A spacer inside the envelope adjacent to the valve inlet aids in preventing the highly flexible vinyl sheet material from immediately collapsing around the valve; collapse which might prevent thorough evacuation of the entire envelope.

More importantly, a heavy paper sheet is folded over to provide a holder within which the film and screen are placed. The fibrous folder assures that there will be complete evacuation and eliminates trapping pockets of air during evacuation.

In use, the intensifier screen and unexposed X-ray film are placed face to face inside the folded over paper holder within the envelope in a darkroom. The operator then slips a clamp along the reinforcing strips at the open edge to seal the envelope. The resultant filled envelope is then taken out of the darkroom and the valve attached to a source of vacuum. After the vacuum has been applied so that the envelope collapses to hold the intensifier screen and X-ray film tightly together, the valve is closed and the vacuum removed. The result is a cassette ready for use.

The normal sealing of the vinyl envelope leaves an interior bead which tends to provide a passage for air from the outside into the envelope. This leakage problem is substantially eliminated by a zero pressure contact heat sealing process for sealing the side edges of the envelope thereby eliminating the bead and the path for air leakage.

BRIEF DESCRIPTION OF THE DRAWINGS

FIG. 1 is a perspective view showing the positioning of the intensifier screen, X-ray film and holder for insertion into the vinyl envelope.

FIG. 2 is a cross-sectional view along the line 2—2 of FIG. 1 showing the screen, film and holder inserted therein and the open edge clamped.

FIG. 3 is a view similar to that of FIG. 2 with the envelope evacuated and thus ready for use.

FIG. 4 is a cross-sectional view along the line 4—4 of FIG. 3.

FIGS. 5 and 6 are cross-sectional views through the valve showing the valve, respectively, open and closed.

FIG. 7 illustrate the method of sealing the sealed edges of the FIG. 1 envelope.

DESCRIPTION OF THE PREFERRED EMBODIMENTS

As shown in the FIGS., an opaque, preferably black, patent plastic envelope 10 has sealed edges 12, 13 and 14. The envelope material can be vinyl, polyethylene or other thermoplastic polymer. The edge 16 is open so that the unexposed X-ray film 18 and the intensifier screen 20 within a folded heavy paper holder 21 can be inserted into the envelope 10 through the mouth of open edge 16. In one embodiment where the intensifier screen and X-ray film is about 10 inches long, the length of the envelope 10 from edge 16 to edge 14 is 12½ inches. The envelope is about 1½ inches wider than the screen 20 and film 18 to facilitate insertion of film and screen.

Two reinforcing strips 22, 23 each ½ inch wide and 50 mil (0.050 inch) thick are sealed to the sheets 10a, 10b of the envelope 10 adjacent to the open edge 16. One strip 22 includes thumb holes 42 to facilitate opening the envelope. After the X-ray film 18 and intensifier screen 20 within the paper folder 21 are placed in the envelope 10 in the darkroom, the operator can simply, by feel, locate the reinforcing strips 22, 23 and slip a plastic C-shaped claim 25 over the strip (see FIGS. 2 and 3) to seal the envelope 10. The plastic out of which the C-clamp 25 is made can be of a resilient material such as polystyrene and dimensioned to provide an interference type fit between clamp 25 and the four plies of strips 22, 23 and envelope sheets 10a, 10b.

The valve 30 is preferably an automatic check-type valve with a standard automobile tire type core 32. The Roberts valve type No. 40-AO has been found effective. It is important that the valve 30 have a stem 34 which maintains its normally closed position until or unless a properly mating vacuum hose coupler is inserted to depress the stem 34 and to hold it depressed while the interior of the envelope 10 is evacuated. Once the evacuation is completed, the removal of the vacuum hose coupler releases the spring-loaded stem 34 into its normally closed position thus assuring an air-tight seal.

The valve 30 is mounted in a vinyl tube 36, which tube 36 in turn is hermetically sealed to the envelope sheets 10a, 10b. A cylindrical vinyl reinforcing insert 38 keeps the vinyl segment from collapsing around the valve 30 when a vacuum is drawn. The vinyl tube 36 is approximately one inch long and provides a finger hold for the technician when connecting the vacuum hose coupler to the threaded portion 40 of the valve 30.

Alternate to the reinforcing tube 38, a sponge filling the vinyl tube 36 inward of the valve 30 can be used to assure that communcations with the interior of the envelope 10 is maintained throughout evacuation.

It is preferable that the width of the envelope 10 be at least one inch greater than the width of the film. This will facilitate loading and unloading and increase the likelihood that the technician will simply drop the film in rather than put his hand into the envelope when loading the envelope.

In use, the operator in a darkroom slips the C-clamp 25 over the open edge 16 to create the condition shown in FIG. 2. Then outside the darkroom the valve 30 is connected to a source of vacuum and the envelope evacuated to the condition shown in FIG. 4. The source of the vacuum is then disconnected and the cassette is ready for use.

After use, the cassette is taken into a darkroom, the C-clamp 28 slipped off, the envelope opened and the folder 21 containing the X-ray film 18 and intensifier screen 20 taken out. The envelope 10 can then be used again, as can the intensifier screen 20 and the above-described operation repeated. Openings 42 in the strip 22 provide a means to facilitate opening the envelope.

As may be seen in FIG. 7, a paired two sheets of 10 mil (0.010 inch) thick vinyl are positioned on a surface 50. Along the side edges 13 and 14, an L-shaped hold down attachment 52 is positioned. The two sheets 10a, 10b of the envelope 10 are each ten mils thick and are polished surface material known in the trade as patent plastic. When ordered as patent plastic, the material comes in a two-sheet thick roll in which the two polished surfaces face one another. An appropriate length of this material is cut and placed on the surface 40. Thus, the two polished surfaces become the interior faces of the envelope 10. Where two ten mil sheets are employed, the hold down fixtures 52 provide a hold down space above the surface 50 of exactly twenty mils so that a nil amount of pressure is exerted on the edges 12 and 13 of the envelope sheets. Heat is then applied through the heat conducting L-shaped hold down fixtures 52 so that the edges 12 and 13 are sealed. The portion of the edge 13 to which the valve 30 is attached is sealed separately. The purpose of this arrangement with respect to the carefully dimensioned hold down and sealing fixtures 52 is to assure that there will be no bead along the inner edges 12 and 13, or, at least, that there will be no such bead along these edges at the portion of the envelope 10 near the open edge 16. Thus, when the open edge 16 is clamped shut, the sheets will lay very flat along the entire length of the open edge 16 and there will be no bridging due to any bead that may exist along the inner side edges 12, 13 and thus the risk of air leaking into the evacuated cassette along such a bridge is substantially eliminated.

The absence of a bead together with the facing interior polished plastic surfaces creates a leak-proof envelope. The vacuum is held because these two features combine to assure no paths for air leakage.

It is believed that these highly-polished facing surfaces are effective to assure a long-lasting vacuum in the cassette because when forced together during evacuation, they adhere to one another so completely as to seal off the portion of the interior of the cassette between open edge 16 and film from the outside air in a fashion that eliminates all possible air paths.

When the facing surfaces are not highly polished, there is no tendency for them to adhere other than that created by the outside pressure exerted when the vacuum is taken. But, to the extent that there are any miniscule air pockets or air paths between the nonpolished facing surfaces, there is provided a path for air to leak in and once such leakage starts, the entire vacuum is rapidly destroyed.

However, the good sealing quality of the polished surfaces creates the problem that during evacuation local air bubbles are formed. Pockets of air can be encapsulated as the vinyl collapses around a local area. This problem arose over the surface of the film 18 or screen 20 when the folder 21 is not used. Thus a roughened surface or fibrous insert has been found necessary to assure air paths during evacuation that eliminate air bubbles and thus assure the desired complete and even evacuation across the entire surface of the film 18 and screen 20.

The heavy paper folder 21 serves this air path providing function. A fibrous, preferably rough surface, material thus prevents the trapping of air bubbles over the surface of the film and/or screen and thus assures a completle and even texture across the whole surface of the screen and film.

A heavy paper folder 21 is a preferred insert because it provides the additional convenience of a folder in which to hold the film and screen and to keep them in line. It is an aid in inserting the film and screen. However, the folder could be eliminated if the intensifier screen 20 were laminated to a cardboard back and two intensifier screens used on either side of the X-ray film as is common practice. The cardboard back would have the same function of providing air paths across the surface of the screen. Accordingly, it should be understood herein that the term insert is used to refer to two ply arrangement which may be, and preferably is, a single folded separable insert.

In one embodiment a 240 weight white coronado texture paper, supplied by the Milton Paper Company of 100 West 22nd Street, New York, N.Y., was used and found effective.

The two reinforcing strips 22, 23 are important to insure a reasonable life for this reusable envelope 10. These reinforcing strips prevent the deformation of the thin collapsible sheets 10a, 10b near the open edge 12. Any such deformation would result in the sheets not lying perfectly flat against one another when closed and thus would prevent providing air tight seal. The reinforcing strips 22, 23 by preventing deformation, assure that the two sheets will lie perfectly flat against one another at the open edge, when closed, and thus serve to assure the obtaining and maintenance of the vacuum after repeated uses of the envelope 10.

What is claimed is:

1. A reuseable envelope for an X-ray cassette having X-ray film and intensifier screen comprising:
    first and second collapsible sheets sealed to one another along first, second and third sealed edges forming an envelope having an open edge, a sealing zone extending across said open edge between said first and second sealed edges, said sheets having polished facing interior surfaces in said sealing zone, said interior surfaces in said sealing zone being flush against each other at the line of the seal at said first and second sealed edges, the seal at said first and second sealed edges being beadless in said sealing zone, and a valve sealed to one of said sealed edges permitting communication between the interior of said envelope and the outside, said valve being positioned away from said sealing zone.

2. The envelope of claim 1 further comprising:

first and second flat insert portions, each of said portions having a surface large enough to substantially cover the surface area of whatever X-ray film and intensifier screen is used, said insert portions providing air paths across the surface of said insert portions to said valve said first and second collapsible sheets being large enough to accomodate said insert portions within said envelope in a position removed from said sealing zone.

3. The envelope of claim 1 further comprising:

a spacer element inside said envelope adjacent to the port of said valve and providing a separation between said sheets of said envelope adjacent said valve.

4. The envelope of claim 2 further comprising:

first and second reinforcing strips along the edge respectively of said first and second collapsible sheets at said open edge.

5. The envelope of claim 4 further comprising:

a resilient C-clamp dimensioned to fit along said reinforcing strips.

6. The envelope of claim 1 further comprising:

first and second reinforcing strips along the edge respectively of said first and second collapsible sheets at said open edge.

7. The envelope of claim 6 further comprising:

a spacer element inside said envelope adjacent to the port of said valve and providing a separation between said sheets of said envelope adjacent said valve.

8. The envelope of claim 6 further comprising:

a resilient C-clamp dimensioned to fit along said reinforcing strips.

9. The method of sealing edges of a two collapsible sheet envelope having an open edge to provide a vacuum retaining cassett for X-ray film and intensifier screen contained therein comprising the steps of:

placing an edge of two sheets of collapsible material having facing polished surfaces between and in contact with heat conducting members at substantially nil pressure, and applying heat to said sheets through said members of seal said edge.

10. The method of claim 9 wherein said sheets are of a thermoplastic polymer.

* * * * *